United States Patent [19]
Morgan, Jr.

[11] Patent Number: 5,853,676
[45] Date of Patent: Dec. 29, 1998

[54] UV SPA AND POOL SANITIZING DEVICE

[76] Inventor: W. Wayne Morgan, Jr., 202 King St., Uxbridge, Ontario, Canada, L9P 1B2

[21] Appl. No.: 955,592

[22] Filed: Oct. 22, 1997

[51] Int. Cl.[6] .................................................. B01J 19/08
[52] U.S. Cl. ........................... 422/186.3; 422/24; 422/25; 422/186; 250/455.11; 250/436; 210/244; 210/748
[58] Field of Search ................... 422/22, 24, 25, 422/186, 186.3; 210/748, 244, 246; 250/455.11, 436

[56] References Cited

U.S. PATENT DOCUMENTS

| | | | |
|---|---|---|---|
| 4,372,860 | 2/1983 | Kaas | 422/24 |
| 4,779,174 | 10/1988 | Staten et al. | 362/158 |
| 5,476,116 | 12/1995 | Price et al. | 422/119 |

*Primary Examiner*—Krisanne Thornton
*Assistant Examiner*—Fariborz Moazzam

[57] ABSTRACT

A pool or spa sterilizing device is provided including a housing having an interior space. An ultra-violet tube is positioned in the interior space of the housing and is adapted to emit ultra-violet radiation upon the receipt of power. A power cord is included having a first end with a standard grounded power plug for being releasably connected with an alternating current receptacle and a second end electrically connected to the ultra-violet tube. As such, power is supplied to the ultra-violet tube upon the plug of the power cord being plugged into the current receptacle.

1 Claim, 2 Drawing Sheets

UV SPA AND POOL SANITIZING DEVICE

BACKGROUND OF THE INVENTION

1. Field of the invention

The present invention relates to pool sanitizers and more particularly pertains to a new UV spa and pool sanitizing device for killing bacteria and other microorganisms within a pool with ultra-violet rays.

2. Description of the Prior Art

The use of pool sanitizers is known in the prior art. More specifically, pool sanitizers heretofore devised and utilized are known to consist basically of familiar, expected and obvious structural configurations, notwithstanding the myriad of designs encompassed by the crowded prior art which have been developed for the fulfillment of countless objectives and requirements.

Known prior art pool sanitizers include U.S. Pat. No. 4,372,860; U.S. Pat. No. 5,068,030; U.S. Pat. No. Des. 331,098; U.S. Pat. No. Des. 331,447; U.S. Pat. No. Des. 350,181; and U.S. Pat. No. 4,752,401.

In these respects, the UV spa and pool sanitizing device according to the present invention substantially departs from the conventional concepts and designs of the prior art, and in so doing provides an apparatus primarily developed for the purpose of killing bacteria and other microorganisms within a pool with ultra-violet rays.

SUMMARY OF THE INVENTION

In view of the foregoing disadvantages inherent in the known types of pool sanitizers now present in the prior art, the present invention provides a new UV spa and pool sanitizing device construction wherein the same can be utilized for killing bacteria and other microorganisms within a pool with ultra-violet rays.

The general purpose of the present invention, which will be described subsequently in greater detail, is to provide a new UV spa and pool sanitizing device apparatus and method which has many of the advantages of the pool sanitizers mentioned heretofore and many novel features that result in a new UV spa and pool sanitizing device which is not anticipated, rendered obvious, suggested, or even implied by any of the prior art pool sanitizers, either alone or in any combination thereof.

To attain this, the present invention generally comprises a housing having a disk-shaped configuration. As shown in the Figures, the housing is equipped with a circular top face, a circular bottom face, and a thin tubular periphery formed therebetween thereby defining an interior space. The housing is preferably constructed from an elastomeric material. For reasons that will become apparent hereinafter, an aperture is formed in the periphery of the housing. Mounted to a central extent of the bottom face of the housing within the interior space thereof is an insulative ballast. Such ballast has a rectangular configuration. Next provided is a generally annular ultra-violet tube having a pair of ends. Coupled to such ends is a pair of conductive rigid parallel mounting arms mounted to the ballast. By this structure, the ultra-violet tube is positioned in the interior space of the housing in concentric relationship therewith. During use, the ultra-violet tube is adapted to emit ultra-violet radiation upon the receipt of power. A power cord is provided with a length of at least 10 feet. The cord is situated through the aperture of the housing. As shown in FIGS. 1 & 2, the power cord has a first end with a standard grounded power plug for being releasably connected with an alternating current receptacle. A second end of the cord is coupled to the ballast and further electrically connected to the conductive arms of the ultra-violet tube within the ballast. As such, power is supplied to the ultra-violet tube upon the plug of the power cord being plugged into the current receptacle. Finally, a grommet is integrally coupled to the power cord and further sealingly secured to the aperture of the housing. The grommet thus serves to preclude the entry of water within the housing. It should be noted that the housing has a mean density less than that of water thereby permitting the housing to float.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new UV spa and pool sanitizing device apparatus and method which has many of the advantages of the pool sanitizers mentioned heretofore and many novel features that result in a new UV spa and pool sanitizing device which is not anticipated, rendered obvious, suggested, or even implied by any of the prior art pool sanitizers, either alone or in any combination thereof.

It is another object of the present invention to provide a new UV spa and pool sanitizing device which may be easily and efficiently manufactured and marketed.

It is a further object of the present invention to provide a new UV spa and pool sanitizing device which is of a durable and reliable construction.

An even further object of the present invention is to provide a new UV spa and pool sanitizing device which is susceptible of a low cost of manufacture with regard to both materials and labor, and which accordingly is then susceptible of low prices of sale to the consuming public, thereby making such UV spa and pool sanitizing device economically available to the buying public.

Still yet another object of the present invention is to provide a new UV spa and pool sanitizing device which provides in the apparatuses and methods of the prior art some of the advantages thereof, while simultaneously overcoming some of the disadvantages normally associated therewith.

Still another object of the present invention is to provide a new UV spa and pool sanitizing device for killing bacteria and other microorganisms within a pool with ultra-violet rays.

Even still another object of the present invention is to provide a new UV spa and pool sanitizing device that includes a housing having an interior space. An ultra-violet tube is positioned in the interior space of the housing and is adapted to emit ultra-violet radiation upon the receipt of power. A power cord is included having a first end with a standard grounded power plug for being releasably connected with an alternating current receptacle and a second end electrically connected to the ultra-violet tube. As such, power is supplied to the ultra-violet tube upon the plug of the power cord being plugged into the current receptacle.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
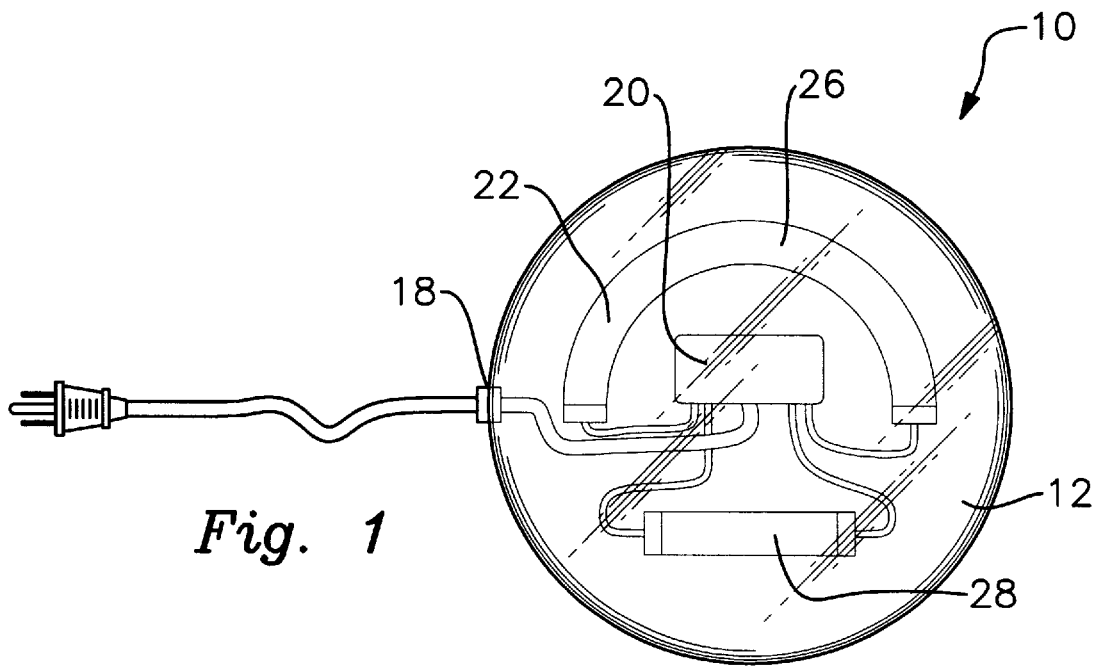
FIG. 1 is a top view of a new UV spa and pool sanitizing device according to the present invention.
Figure 2:
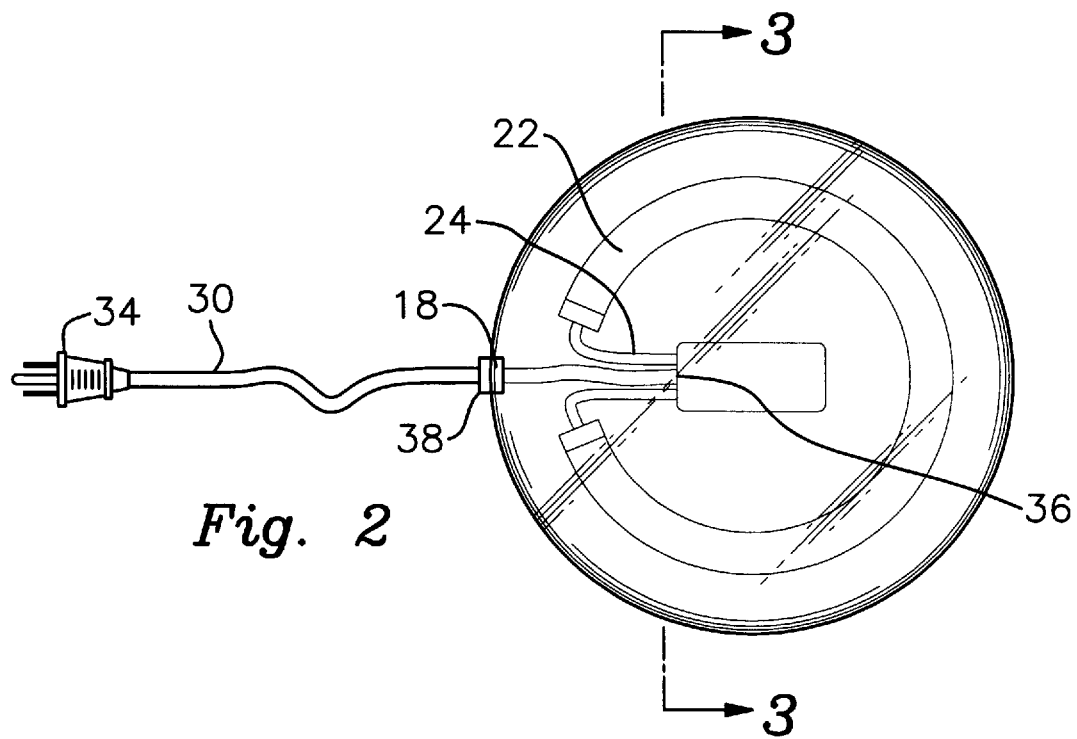
FIG. 2 is a top view of an alternate embodiment of the present invention.
Figure 3:
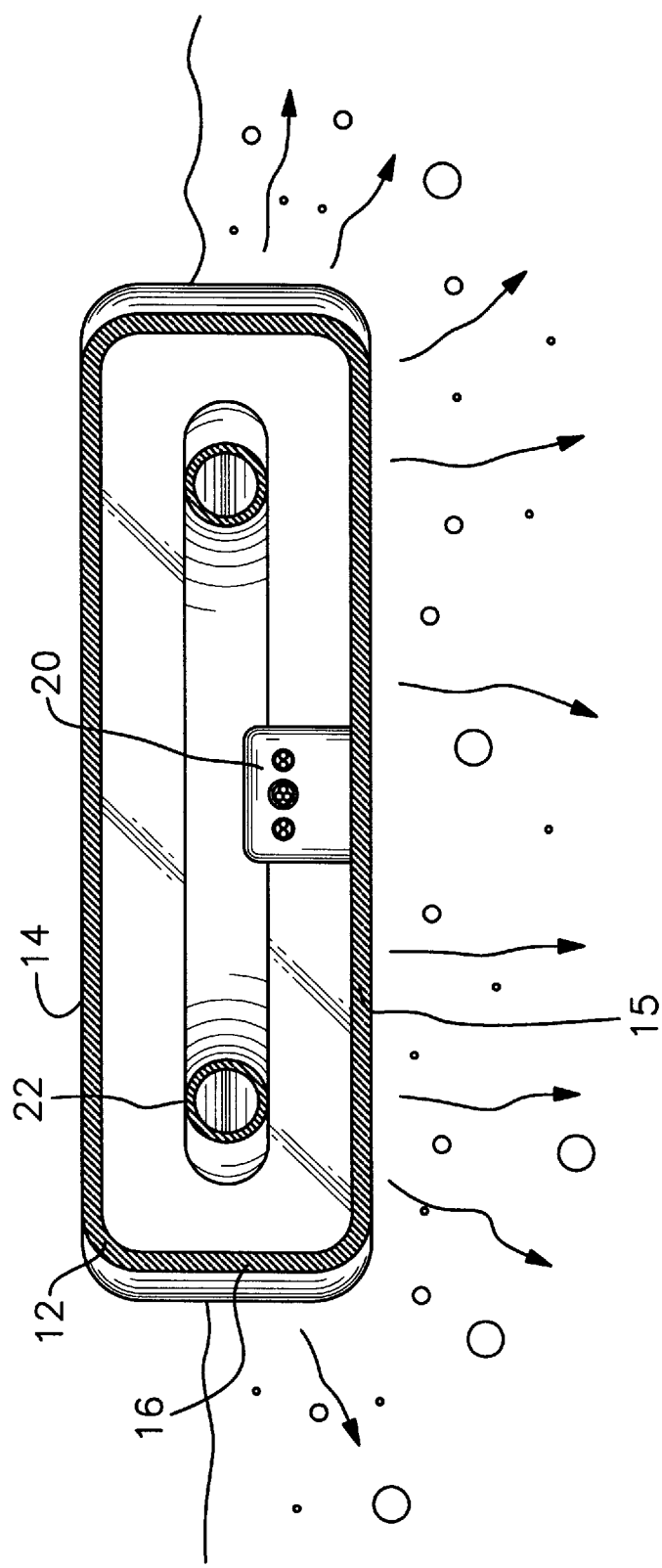
FIG. 3 is a cross-sectional view of the present invention taken along 3—3 shown in FIG. 2.

With reference now to the drawings, and in particular to FIGS. 1 through 3 thereof, a new UV spa and pool sanitizing device embodying the principles and concepts of the present invention and generally designated by the reference numeral 10 will be described.

The present invention, as designated as numeral 10, includes a housing 12 having a disk-shaped configuration. As shown in the Figures, the housing is equipped with a circular top face 14, a circular bottom face 15, and a thin tubular periphery 16 formed therebetween thereby defining an interior space. The housing is ideally constructed from an elastomeric material. In the preferred embodiment, the material comprises of fuse silica. For reasons that will become apparent hereinafter, an aperture 18 is formed in the periphery of the housing.

Mounted to a central extent of the bottom face of the housing within the interior space thereof is an insulative ballast 20. Such ballast has a rectangular configuration.

Next provided is a generally annular ultra-violet tube 22 having a pair of ends. Coupled to such ends is a pair of conductive rigid parallel mounting arms 24 which are, in turn, mounted to the ballast. Ideally, the arms are covered by an elastomeric lining. By this structure, the ultra-violet tube is positioned in the interior space of the housing in concentric relationship therewith. During use, the ultra-violet tube is adapted to emit ultra-violet radiation upon the receipt of power.

In an alternate embodiment, as shown in FIG. 1, the ultra-violet tube includes a C-shaped tube 26 mounted to the ballast. Further, an additional linear tube 28 is mounted to the ballast opposite of the C-shaped tube.

A power cord 30 is provided with a length of at least 10 feet. The cord is situated through the aperture of the housing. As shown in FIGS. 1 & 2, the power cord has a first end with a standard grounded power plug 34 for being releasably connected with an alternating current receptacle. Such receptacle preferably comprises a GFI outlet. A second end 36 of the cord is coupled to the ballast and further electrically connected to the conductive arms of the ultra-violet tube within the ballast. Such is accomplished by way of a pair of conduits formed in the ballast. As such, power is supplied to the ultra-violet tube upon the plug of the power cord being plugged into the current receptacle.

Finally, a grommet 38 is integrally coupled to the power cord and further sealingly secured to the aperture of the housing. The grommet thus serves to preclude the entry of water within the housing. It should be noted that the housing has a mean density that is less than that of water thereby permitting the housing to float. In the alternative, a weight may be coupled to the housing for allowing it to be situated on a floor of the body of water.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pool or spa sterilizing device comprising, in combination:

a housing having a disk-shaped configuration with a circular top face, a circular bottom face, and a tubular periphery formed therebetween thereby defining an interior space, the housing being constructed from an elastomeric material including fuse silica and having an aperture formed in the periphery thereof;

an insulative ballast having a rectangular configuration coupled to a central extent of the bottom face of the housing within the interior space thereof;

a generally annular ultra-violet tube having a pair of ends with a pair of conductive rigid parallel mounting arms mounted to the ballast such that the ultra-violet tube is positioned in the interior space of the housing in concentric relationship therewith, wherein the ultra-violet tube emits ultra-violet radiation upon the receipt of power, the arms being covered with an elastomeric lining;

a power cord with a length of at least 10 feet and situated through the aperture of the housing, the power cord having a first end with a standard grounded power plug for being releasably connected with an alternating current receptacle and a second end coupled to the ballast and further electrically connected to the conductive arms of the ultra-violet tube within the ballast via a pair of conduits formed in the ballast, whereby power is supplied to the ultra-violet tube upon the plug of the power cord being plugged into the current receptacle; and a grommet integrally coupled to the power cord and further sealingly secured to the aperture of the housing for precluding the entry of water within the housing;

whereby the housing has a mean density less than that of water thereby permitting the housing to float.

\* \* \* \* \*